United States Patent [19]
Sokal

[11] Patent Number: 5,885,601
[45] Date of Patent: Mar. 23, 1999

[54] USE OF MACROLIDE ANTIBIOTICS FOR NONSURGICAL FEMALE STERILIZATION AND ENDOMETRIAL ABLATION

[75] Inventor: David C. Sokal, Mebane, S.C.

[73] Assignee: Family Health International, Durham, N.C.

[21] Appl. No.: 832,782

[22] Filed: Apr. 4, 1997

Related U.S. Application Data

[60] Provisional application No. 60/014,923 filed Apr. 5, 1996.
[51] Int. Cl.$^6$ .................................................. A01N 25/00
[52] U.S. Cl. .......................... 424/405; 424/408; 424/422; 424/430; 424/433; 424/489; 514/29; 514/30
[58] Field of Search ................................ 514/27, 28, 29, 514/30, 31; 424/405, 408, 417, 427, 430, 433, 436, 464, 489

[56] References Cited

U.S. PATENT DOCUMENTS

| | | | |
|---|---|---|---|
| 4,158,050 | 6/1979 | Zipper | 424/14 |
| 4,185,618 | 1/1980 | Corey | 128/1 R |
| 5,095,917 | 3/1992 | Vancaillie | 128/831 |

FOREIGN PATENT DOCUMENTS 0 114 003  7/1984  European Pat. Off. .

OTHER PUBLICATIONS

Paul Carvalho et al., "Effects of Erythromycin on the Rabbit Pleura: Its Potential Role as a Pleural Sclerosant," *Am. J. Respir Crit Case Med.,* vol. 151, pp. 1228–1232 (1995).

A.A. Joseph et al., "Toxic and antifertility effects of quinacrine hydrochloride in rats," *Amer. J. Obst. and Gynecology,* vol. 119, pp. 978–981 (1974).

Raymond W. KE et al., "Endometrial ablation to control excessive uterine bleeding," *Human Reprod.,* vol. 6, No. 4, pp. 574–579, (1991).

J. Zipper et al., "The Clinical Efficacy of the Repeated Transcervical Instillation of Quinacrine for Female Sterilization," *Int. J. Cynaecol. Obstet.,* 14:499–502 (1976).

Dušanka Radivojević et al., "The Effect of Erythromycin on Fertility of Female Mice and Survival of Their Fetuses", *Genetika,* vol. 11, No. 1, pp. 41–44 (1979).

Katz et al., "Fertility in Adolescent Women Previously Treated for Genitourinary Chlamydial Infection", *Adolescent PediatricGynecology,* vol. 7, No. 3, pp. 147–152 (1994).

*Primary Examiner*—Neil S. Levy
*Attorney, Agent, or Firm*—Finnegan, Henderson, Farabow, Garrett & Dunner, L.L.P.

[57] ABSTRACT

The present invention relates to a method of female sterilization including delivery of a macrolide antibiotic or a pharmacologically acceptable salt of a macrolide antibiotic to the uterine cavity or fallopian tube of the female. The present invention also relates to a method of endometrial ablation including delivery of a macrolide antibiotic or a pharmacologically acceptable salt of a macrolide antibiotic to the uterine cavity of a female. The endometrial ablation effected in this manner may be used to treat the conditions of excessive menstrual bleeding or menstrual pain in women. A preferred macrolide antibiotic is erythromycin, or its pharmacologically acceptable salts.

28 Claims, No Drawings

USE OF MACROLIDE ANTIBIOTICS FOR NONSURGICAL FEMALE STERILIZATION AND ENDOMETRIAL ABLATION

This application is based on research conducted under contract with the United States Agency for International Development, Contract No. AID/CCP-3079-A-5022-00.

This application is also based on United States Provisional Application No. 60/014,923, filed Apr. 5, 1996, from which Applicant claims the benefits of priority under 35 U.S.C. § 119(e)(1).

FIELD OF THE INVENTION

The present invention relates to a method of female sterilization by the administration of a macrolide antibiotic. More particularly, the present invention relates to a method of female sterilization by the intrauterine administration of erythromycin. The present invention further relates to a method of administering a macrolide antibiotic, particularly erythromycin, for the purpose of endometrial ablation.

BACKGROUND OF THE INVENTION

A number of researchers have worked to identify a simple and inexpensive method of non-surgical female sterilization. The advantages of a non-surgical sterilization procedure may include easier access to treatment for the patient and increased safety.

One such method that has been developed uses quinacrine pellets, and has been evaluated relative to the two potential advantages noted above. U.S. Pat. No. 4,158,050, the entire contents of which Applicant incorporates herein by reference, discloses the delivery of a solid pellet of quinacrine to the uterine cavity. It is believed that the quinacrine, once located within the uterine cavity, causes fibrosis of the fallopian tubes. Such fibrosis, in turn, prevents pregnancy.

The quinacrine method has shown that a non-surgical method can provide patients with easier access to the treatment, because the delivery of the solid quinacrine pellet is similar to an IUD-insertion, and can be done by paramedical personnel. Sterilization with quinacrine therefore does not require an operating room, and can be done as an outpatient procedure.

While data on quinacrine suggest that it is safer in the short term than surgery, certain researchers have raised issues concerning long-term safety, including the possibility of (1) mutagenicity, (2) carcinogenicity, (3) and increased ectopic pregnancies.

Researchers have also focused their efforts on the treatment of excessive menstrual blood loss and excessive menstrual pain. Excessive menstrual blood loss and pain account for a large number of hysterectomies performed in women in the fourth and fifth decades of life. Management of these conditions in the past has included destruction of the endometrium to induce amenorrhoea. As stated in Ke et al., "Endometrial Ablation to Control Excessive Uterine Bleeding," *Human Reproduction*, Vol. 6, No. 4, pp. 574–80 (1991), destruction of the endometrium has been attempted cryocoagulation and a variety of other methods. Most of these methods, however, have been abandoned due to a lack of uniformity in the results and potential risks involved.

Currently, endometrial ablation is achieved by surgical procedures. Specifically, laser ablation or electrosurgical resection of the endometrium is performed with the aid of an hysteroscope. These procedures, used for the treatment of excessive menstrual bleeding or menstrual pain, may cause several risks associated with the invasive nature of the surgery. For example, use of the hysteroscope may lead to hemorrhage, absorption of distending media, and accidental perforation of the uterus. Further, these surgical procedures require anesthesia, the use of an operating room, and/or expensive and complex equipment.

SUMMARY OF INVENTION

It is therefore an object of the present invention to overcome the foregoing and other difficulties encountered in the prior art.

Another object of the present invention is to provide a non-surgical sterilization procedure for women.

Another object of the present invention is to provide a non-surgical sterilization procedure for women with a minimized risk of systemic toxic effects, mutagenicity, carcinogenicity, or ectopic pregnancy.

Another object of the present invention is to provide a method of endometrial ablation that prevents or reduces the occurrence of excessive menstrual bleeding or menstrual pain in women.

To achieve the objects and in accordance with the invention, as embodied and broadly described herein, the present invention relates to a method of female sterilization by delivery of a macrolide antibiotic or a pharmacologically acceptable salt of a macrolide antibiotic to the uterine cavity or fallopian tube of the female.

The invention additionally relates to a method of female sterilization including delivery of a macrolide antibiotic or a pharmacologically acceptable salt of a macrolide antibiotic to the uterine cavity or fallopian tube of a female.

Additional objects and advantages of the invention will be set forth in the description that follows and will be obvious from the description. The foregoing general description and the following detailed description are exemplary and explanatory only and are not restrictive of the claimed invention.

DETAILED DESCRIPTION OF THE INVENTION

The term macrolide antibiotics, as used herein, refers to antibiotics containing a macrocyclic lactone ring. A macrocyclic lactone ring, as used herein, refers to a ring having a lactone moiety and more than seven carbon atoms.

As is known, erythromycin is an example of a macrolide antibiotic. Erythromycin has the formula $C_{37}H_{67}NO_{13}$, and has at least three structural forms. These forms are known as erythromycin A, erythromycin B, and erythromycin C. As used herein, the term "erythromycin" generically refers to all forms of erythromycin. Erythromycin A has a long history of use as an antibiotic.

Macrolide antibiotics, or their pharmacologically acceptable salts, may now be used as an agent to effect female sterilization or endometrial ablation. More specifically, macrolide antibiotics having fibrotic properties may be administered for the purpose of causing female sterilization or endometrial ablation. Such macrolide antibiotics may include, for example, erythromycin, spiramycin, clarithromycin, roxithromycin, and azithromycin.

A particularly preferred macrolide antibiotic for female sterilization or endometrial ablation is erythromycin A. Erythromycin A, at the doses used in connection with the present invention, provides advantages in that it has no known systemic toxicity, mutagenic effects, or teratogenic effects.

The macrolide antibiotic may be administered as a solid pellet, powder, gel, or suspension deposited within the uterine cavity or fallopian tubes. In any of these forms, a typical dosage may be equivalent to about 50 to about 1000 milligrams of erythromycin base. A more preferred dosage may be equivalent to about 250 to about 500 milligrams of erythromycin base. The dosage may be administered in a single composition all at once, or the same dose may be given over the course of several administrations during the course of treatment.

Whether administering the macrolide antibiotic for female sterilization or endometrial ablation, an object of the invention is to achieve the desired result after only one treatment. However, treatment embraced by the present invention may be conducted more than once over time. For example, when administered as a sterilization procedure, women aged less than 30 to 35 years of age may need two or three treatments to reliably achieve sterility. On the other hand, women aged more than 30 to 35 years of age may need only one or two treatments to reliably achieve sterility. The most preferred number of treatments needed, along with the most preferred dosages, may further be readily determined by data from animal studies or clinical trials in women.

The macrolide antibiotic may be administered in the form of a base or in the form of its pharmacologically acceptable salts. The salts may be preferred due to their solubility characteristics. For example, two such erythromycin salts, currently marketed for intravenous formulations having use as an antibiotic, are the gluceptate and lactobionate salts. Other salts may include the stearate, estolate, or ethyl succinate salts, and their pharmacologically acceptable equivalents.

The macrolide antibiotic may also be administered in combination with certain adjuvants to enhance the efficacy of the drug. For example, adjuvants such as copper, antiprostaglandins, betamethasone or other steroidal compounds, and ibuprofen or other non-steroidal prostaglandins may improve the efficacy of the sterilization procedure. Similarly, where the macrolide antibiotic is administered as a solid pellet, sodium thiopental may also be administered to improve intrauterine retention of the pellet.

In addition to the administration of the macrolide antibiotic, an intramuscular dose of about 150 milligrams of depot-medroxyprogesterone acetate (DPMA) may be given to suppress growth and/or regrowth of the endometrium. While DPMA is a preferred agent for this purpose due to its low cost, other agents may also be used, such as danazol or GnRH analogues such as goserelin.

Any of the above-mentioned agents that are administered in order to suppress endometrial growth may be given for a period of one or more weeks or months prior to the treatment procedure (intrauterine administration of a macrolide antibiotic). Alternatively, their administration may begin at the time of the treatment procedure and continue for a period of one or more weeks or months after the treatment procedure.

A preferred embodiment of the invention embraces depositing the macrolide antibiotic as a solid pellet in a manner similar to that well known and used to deliver an intrauterine device ("IUD") for use. Typically, a method of depositing the macrolide antibiotic, for example an erythromycin pellet, may include first placing the erythromycin, pressed into the shape of a pellet, in a plastic tube with a push rod being positioned behind the pellet. The tube is then passed through the cervical canal and inner ostium until the uterine fundus is reached. At this point, the push rod is held stationary and the tube is pulled back over the push rod to expel the pellet into the uterine cavity. After the pellet has been discharged, the insertion device is, of course, removed.

The erythromycin pellet is desirably substantially in the shape of a cylinder. To avoid the need for dilating the cervix during insertion, the pellet diameter should be less than 4 millimeters, with about 3.5 millimeters being preferred. Desirably, the erythromycin pellet is compacted to contain about 3 to about 10 milligrams of erythromycin per millimeter of length. While each pellet may contain the entire intended dosage, it is preferred to split the dosage between two or more pellets for administration.

To minimize or avoid the occurrence of peritoneal spillage, the erythromycin pellet should have a profile with respect to speed of dissolution and osmotic load that is similar to current quinacrine formulations for sterilization procedures. For example, the dissolution half life of the erythromycin pellet may preferably be about ten minutes.

Such a pellet may readily be made by one of ordinary skill in the art, selecting the appropriate salt of the erythromycin, and a preferred combination of inactive ingredients. These inactive ingredients are well known in the art, and include for example, polyethylene glycol as a binder. The erythromycin pellet may further contain lubricants, such as magnesium sulfate, which permit the erythromycin pellet to be easily removed from a pellet compressing machine.

While administration of the macrolide antibiotic as a solid pellet is preferred, other dosage forms of administration may be used such as a powder, gel, or suspension. Numerous suitable types of gels or suspensions may be used by those having ordinary skill in the art, based on well known carrier chemicals such as methylcellulose, dextran, carrageenan, polycarbophil, and carbopol resins such as Carbomer 934P. Examples of such carrier chemicals may be found in U.S. Pat. No. 4,185,618, the entire contents of which are incorporated herein by reference.

Regardless of the dosage form of the macrolide antibiotic, an advantage of the present invention embraces the "blind administration" of the macrolide antibiotic while maintaining a relatively high efficacy. As used herein, the term "blind administration" refers to an administration method that does not require localization of the antibiotic in or near the tubal ostia. The method of blind administration thus decreases the need for highly trained medical personnel to perform the method.

However, the present invention also embraces the administration of macrolide antibiotics to specifically targeted regions of the uterine cavity or fallopian tubes. For example, rather than using a blind administration technique similar to an IUD insertion, the macrolide antibiotic may be placed near the tubal ostia or directly into the fallopian tubes using an existing or modified hysteroscope or falloposcopic device.

EXAMPLE 1

Sterilization is conducted by insertion into the uterus of cylindrical pellets. The pellets are of a size permitting their insertion with the use of an IUD inserter. To achieve the needed total dose, without pellets that are too long, seven or eight pellets are used. Each pellet, formulated to dissolve with a half-life of about 10 to about 20 minutes, has the following composition:

Erythromycin base–30 to 40 mg

Additional inactive ingredients are used by those skilled in the art to facilitate the production and proper dissolution of the pellets. Agents such as magnesium stearate and polyethylene glycol are commonly used for such purposes by those skilled in the art of preparing pharmacological formulations.

Immediately preceding or following the uterine insertion of the pellets, the patient receives an injection of 150 mg of depot medroxyprogesterone.

I claim:

1. A method of female sterilization comprising delivery of a macrolide antibiotic or a pharmacologically acceptable salt of a macrolide antibiotic directly to the uterine cavity or fallopian tube of the female in an amount effective to cause sterilization.

2. The method of claim 1, wherein the female is a mammal.

3. The method of claim 1, wherein the macrolide antibiotic is selected from the group consisting of erythromycin, spiramycin, clarithromycin, roxithromycin, and azithromycin.

4. The method of claim 1, wherein the macrolide antibiotic is erythromycin A or a pharmacologically acceptable salt of erythromycin A.

5. The method of claim 1, wherein the pharmacologically acceptable salt is selected from the group consisting of erythromycin gluceptate, erythromycin lactobionoate, erythromycin stearate, erythromycin estolate, and erythromycin ethyl succinate.

6. The method of claim 3, wherein the macrolide antibiotic or its pharmologically acceptable salt, is delivered in a dosage which is equivalent to about 50 to about 1000 milligrams of erythromycin base.

7. The method of claim 1, wherein the macrolide antibiotic or its pharmacologically acceptable salt is delivered in sequential stages.

8. The method of claim 1, comprising administration of the macrolide antiobiotic or its pharmacologically acceptable salt to the uterine fundus without requiring localization near the tubal ostia.

9. The method of claim 1, wherein the macrolide antibiotic or its pharmacologically acceptable salt is delivered as a powder, gel, or suspension.

10. The method of claim 1, wherein the macrolide antibiotic or its pharmacologically acceptable salt is delivered as a solid pellet.

11. The method of claim 1, further comprising the administration of an adjuvant selected from the group consisting of hormonal agents, antiprostaglandins, steroidal compounds, and combinations thereof.

12. The method of claim 1, further comprising the administration of an adjuvant selected from the group consisting of copper, betamethasone, ibuprofen, depot-medroxyprogesterone, goserelin, danazol, and combinations thereof.

13. A method of endometrial ablation comprising delivery of a macrolide antibiotic or a pharmacologically acceptable salt of a macrolide antibiotic directly to the uterine cavity or fallopian tube of a female.

14. The method of claim 13, wherein the female is a mammal.

15. The method of claim 13, wherein the macrolide antibiotic is selected from the group consisting of erythromycin, spiramycin, clarithromycin, roxithromycin, and azithromycin.

16. The method of claim 13, wherein the macrolide antibiotic is erythromycin A or a pharmacologically acceptable salt of erythromycin A.

17. The method of claim 13, wherein the pharmacologically acceptable salt is selected from the group consisting of erythromycin gluceptate, erythromycin lactobionoate, erythromycin stearate, erythromycin estolate, and erythromycin ethyl succinate.

18. The method of claim 13, wherein said endometrial ablation prevents or reduces menstrual bleeding in the female.

19. The method of claim 13, wherein said endometrial ablation prevents or reduces menstrual pain in the female.

20. The method of claim 13, wherein the erythromycin or its pharmacologically acceptable salt is delivered as a powder, gel, or suspension.

21. The method of claim 13, wherein the erythromycin or its pharmacologically acceptable salt is delivered as a pellet.

22. The method of claim 13, wherein the erythromycin or its pharmacologically acceptable salt is delivered in an amount effective to prevent or reduce menstrual bleeding in the female.

23. The method of claim 13, wherein the erythromycin or its pharmacologically acceptable salt is delivered in an amount effective to prevent or reduce menstrual pain in the female.

24. The method of claim 13, further comprising the administration of an adjuvant selected from the group consisting of hormonal agents, antiprostaglandins, steroidal compounds, and combinations thereof.

25. The method of claim 13, further comprising the administration of an adjuvant selected from the group consisting of copper, betamethasone, ibuprofen, depot-medroxyprogesterone, goserelin, danazol, and combinations thereof.

26. The method of claim 13, wherein the macrolide antibiotic or pharmacologically acceptable salt thereof is administered by a non-surgical method.

27. The method of claim 1, wherein the macrolide antibiotic or pharmacologically acceptable salt thereof is administered by a non-surgical method.

28. The method of claim 6, wherein the dosage is equivalent from about 250 to about 500 milligrams of erythromycin base.

* * * * *